United States Patent [19]
Anderson

[11] 4,184,943
[45] Jan. 22, 1980

[54] FRACTIONATION IN AN ADSORPTIVE HYDROCARBON SEPARATION PROCESS

[75] Inventor: Mark C. Anderson, Palatine, Ill.

[73] Assignee: UOP Inc., Des Plaines, Ill.

[21] Appl. No.: 972,113

[22] Filed: Dec. 21, 1978

[51] Int. Cl.$^2$ .................... C07C 7/13; C10G 25/00
[52] U.S. Cl. .................... 208/310 R; 203/41; 585/826
[58] Field of Search .................... 208/310 R, 310 Z; 260/676 MS; 203/41

[56] References Cited

U.S. PATENT DOCUMENTS

| | | | |
|---|---|---|---|
| 3,291,726 | 12/1966 | Broughton | 208/310 R |
| 3,455,815 | 7/1969 | Fickel | 208/310 R |
| 4,006,197 | 2/1977 | Bieser | 260/676 MS |

Primary Examiner—Herbert Levine
Attorney, Agent, or Firm—James R. Hoatson, Jr.; John F. Spears, Jr.; William H. Page, II

[57] ABSTRACT

A hydrocarbon separation process which includes a novel method of fractionating the extract and raffinate streams removed from a simulated moving bed of a selective adsorbent. The extract and raffinate streams are passed into separate fractionation columns, each having a sidecut removed above the feed point. Each sidecut is stripped, with the stripper overhead vapor passing directly into the extract or raffinate column. The bottoms streams of the two sidecut strippers are combined and passed into the adsorbent bed.

6 Claims, 1 Drawing Figure

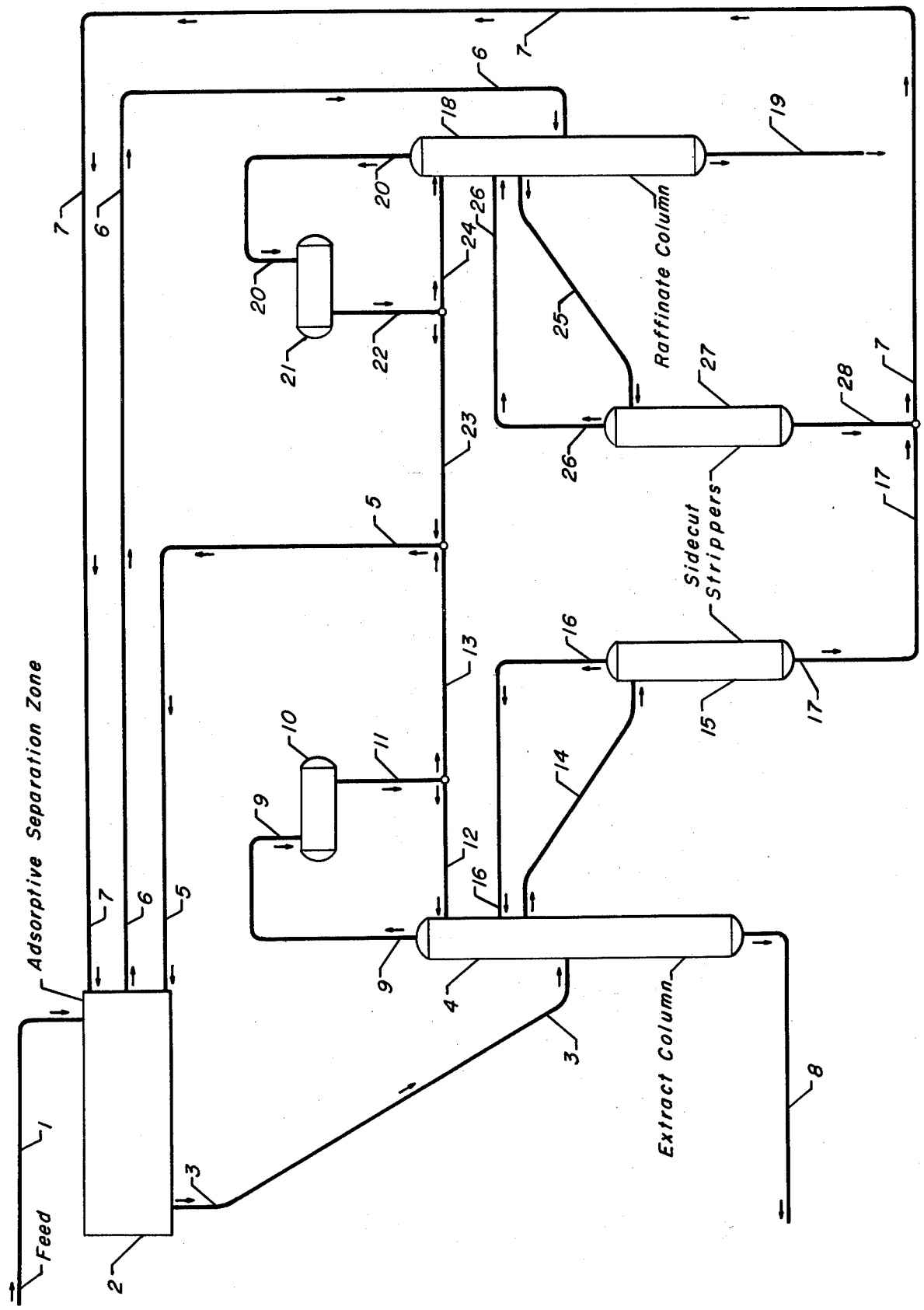

FRACTIONATION IN AN ADSORPTIVE HYDROCARBON SEPARATION PROCESS

FIELD OF THE INVENTION

The invention relates in general to a process for separating hydrocarbons or hydrocarbonaceous chemical compounds. The invention more directly concerns a process for separating hydrocarbons through the use of a selective sorbent which is preferably a crystalline aluminosilicate. The invention is specifically concerned with the fractionation of the extract, raffinate and desorbent streams used in a process for the adsorptive separation of normal paraffinic hydrocarbons from a mixture which also contains isoparaffinic and aromatic hydrocarbons.

PRIOR ART

The separation of chemical compounds is an important step in many petrochemical and chemical processes and is often performed as an independent operation to recover a product from a multi-component feed stream. Separatory processes have therefore reached a high degree of development. Examples of separatory processes employing a bed of a solid sorbent for separating normal or straight chain paraffinic hydrocarbons from a mixture which also contains iso and/or cyclic hydrocarbons are described in U.S. Pat. Nos. 2,920,037 (Cl. 208–310) and 2,957,927 (Cl. 260–676).

Several commercial hydrocarbon separation processes utilize a simulated moving bed of a solid adsorbent. The operation of a simulated moving bed is well described in U.S. Pat. Nos. 2,985,589 (Cl. 210–34); 3,201,491 (Cl. 260–676); 3,291,726 (Cl. 208∝310); and 3,732,325 (Cl. 260–674SA).

Methods of fractionating the extract and raffinate streams of a simulated moving bed adsorptive separation process are presented in U.S. Pat. Nos. 3,455,815 (Cl. 208–310) issued to R. G. Fickel and 4,006,197 (Cl. 260–676MS) issued to H. J. Beiser. The latter reference is specific to the separation of normal paraffins from isoparaffins using a multi-component desorbent.

BRIEF SUMMARY OF THE INVENTION

The invention provides an improved process for the separation of hydrocarbons using a simulated moving bed of selective adsorbent. The separation of the desorbent hydrocarbons from the extract and raffinate streams is performed in a manner which better utilizes the heat formerly rejected by condensation of the overhead vapor stream of a desorbent splitter column.

One embodiment of the invention may be broadly characterized as comprising the steps of passing a feed stream comprising $C_9$ to $C_{14}$ isoparaffins, co-boiling aromatics and co-boiling normal paraffins into a fixed bed of a solid adsorbent which preferentially adsorbs the normal paraffins and the co-boiling aromatics at a first point; passing a flush stream comprising a first and a second hydrocarbon into the bed of adsorbent at a second point; passing a desorbent stream comprising the second hydrocarbon and a third hydrocarbon into the bed of adsorbent at a third point; withdrawing an extract stream comprising the normal paraffin, the first, the second and the third hydrocarbons from the bed of adsorbent at a fourth point; withdrawing a raffinate stream comprising the isoparaffinic hydrocarbons, the aromatic hydrocarbons, the first, the second and the third hydrocarbons from the bed of adsorbent at a fifth point; simulating the utilization of a moving bed of adsorbent by maintaining a net fluid flow through the bed of adsorbent and periodically moving the first through fifth points in a unidirectional pattern; fractionating the extract stream in a first fractionation column into a first overhead fraction comprising the second and the third hydrocarbons, a first sidecut fraction comprising the first, the second and the third hydrocarbons and a first bottoms fraction comprising the normal paraffins; separating the first sidecut fraction in a first stripping column into a second bottoms fraction comprising the first and the second hydrocarbons and a first overhead vapor stream which is passed into an intermediate point of the first fractionation column; fractionating the raffinate stream in a second fractionation column into a second overhead fraction comprising the second and the third hydrocarbons, a second sidecut fraction comprising the first, the second and the third hydrocarbons and a third bottoms comprising the isoparaffins and co-boiling aromatics; separating the second sidecut fraction in a second stripping column into a fourth bottoms fraction comprising the first and the second hydrocarbons and a second overhead vapor stream which is passed into an intermediate point of the second fractionation column; admixing at least a portion of each of the third and fourth bottoms fractions to form the flush stream passed into the bed of adsorbent; and admixing at least a portion of each of the first and second overhead fractions to form the desorbent stream passed into the bed of adsorbent.

DESCRIPTION OF THE DRAWING

The drawing illustrates the preferred embodiment of the invention. For clarity in describing the inventive concept, various subsystems and apparatus associated with the operation of the process have not been shown. These items include flow and pressure control valves, pumps, temperature and pressure monitoring systems, reactor internals, etc., which may be of customary design. This representation of the preferred embodiment is not intended to exclude from the scope of the inventive concept those other embodiments which are the result of reasonable and normal modification of the preferred embodiment.

Referring now to the drawing, a feed stream comprising a mixture of both iso- and normal $C_{10}$ to $C_{14}$ paraffins enters the process through line 1. The feed stream also contains co-boiling aromatic hydrocarbons. The fed stream is passed through at least a portion of a fixed bed of crystalline aluminosilicates which selectively adsorb normal paraffins. Preferably, this bed of aluminosilicates is operated in a manner which simulates the use of a moving bed adsorption system in which the feed stream passes through only a portion of the entire bed of adsorbent referred to as an adsorption zone. The location of the adsorption zone is gradually shifted through the entire fixed bed to allow the continuous and simultaneous adsorption and desorption of the normal paraffins to occur at different points within the fixed bed of adsorbent.

A liquid stream referred to herein as an extract stream and comprising the preferentially adsorbed normal paraffins of the feed stream and some components of the desorbent stream and the flush stream used in the process is removed from the adsorptive separation zone 2 in line 3 and passed into an extract fractionation column 4. This fractionation column is maintained at conditions effective to separate the entering extract stream into a net bottoms stream removed in line 8 and an overhead vapor stream removed in line 9. The net bottoms stream comprises the normal paraffins which were removed from the feed stream in the adsorptive separation zone and is substantially free of the other hydrocarbons present in the extract stream. The overhead vapor stream of the extract column is passed through a condenser not shown and is then directed into an overhead receiver 10. The liquid which collects in this overhead receiver is removed in line 11 and divided into a first portion which is returned to the extract column as reflux in line 12 and a second portion removed in line 13.

A liquid sidecut stream is removed from an intermediate point of the extract column in line 14. This stream is passed into an upper portion of a sidecut stripper column 15. This sidecut stripper is operated at conditions effective to remove substantially all of the lightest hydrocarbon component of the desorbent stream from the entering sidecut material. In the preferred embodiment, this light component is normal pentane. The overhead vapors of the sidecut stripper are passed into an intermediate point of the extract column 4 through line 16 to aid in the separation performed in the extract column. A net bottoms stream comprising $C_8$ isoparaffins and $C_8$ aromatic hydrocarbons is removed from the sidecut stripper in line 17.

A liquid stream referred to herein as a raffinate stream is removed from the adsorptive separation zone in line 6. This stream comprises isoparaffins which were not preferentially adsorbed, co-boiling aromatic hydrocarbons and also the three hydrocarbon components of the desorbent stream and the flush stream. The raffinate stream is passed into a fractionation column 18 referred to as a raffinate column. This column is operated under conditions effective to separate the entering materials into a net bottoms stream comprising the higher boiling isoparaffins and co-boiling aromatics removed in line 19 and an overhead vapor stream removed in line 20. The overhead vapor stream is passed through a condenser not shown and into an overhead receiver 21. The liquid collected in this overhead receiver is withdrawn through line 22 and separated into a first portion which is returned to the raffinate column in line 24 as reflux and a second portion removed in line 23.

The hydrocarbon streams flowing through lines 13 and 23 are combined to form the desorbent stream which is passed into the adsorptive separation zone 2 through line 5.

A liquid sidecut stream comprising the three hydrocarbon components of the desorbent stream and the flush stream is removed from the raffinate column 18 through line 25. This sidecut stream is passed into an upper portion of a sidecut stripper 27 which is operated at conditions effective to reject substantially all of the entering lightest hydrocarbon component back to the raffinate column as a component of an overhead vapor stream passed through line 26. This overhead vapor stream is passed into an intermediate point of the raffinate column to aid in the separation performed in the upper portion of the column. A net bottoms stream comprising the $C_8$ aromatic hydrocarbon and the $C_8$ isoparaffin is removed from the sidecut stripper 27 in line 28 and admixed with the net bottoms stream removed from the sidecut stripper 15. This combined stream is returned to the adsorptive separation zone through line 7 to be utilized as the flush stream which is passed through portions of the adsorbent bed.

DETAILED DESCRIPTION

The separation of various hydrocarbonaceous compounds through the use of selective adsorbents is widespread in the petroleum, chemical and petrochemical industries. Adsorption is often utilized when it is more difficult or expensive to separate the same compounds by other means such as fractionation. Examples of the types of separations which are often performed using selective adsorbents include the separation of ethylbenzene from a mixture of xylenes, unsaturated fatty acids from saturated fatty acids, fructose from glucose, acyclic olefins from acyclic paraffins, and normal paraffins from isoparaffins. Typically, the selectively adsorbed materials have the same number of carbon atoms per molecule as the non-selectively adsorbed materials and very similar boiling points. Another common application is the recovery of a particular class of hydrocarbons from a broad boiling point range mixture of two or more classes of hydrocarbons. An example is the separation of $C_{10}$ to $C_{14}$ normal paraffins from a mixture which also contains $C_{10}$ to $C_{14}$ isoparaffins.

Adsorptive separation processes require the sequential performance of three basic steps. The adsorbent must first be brought into contact with a feed stream comprising the particular compounds to be collected at adsorption-promoting conditions. This adsorption step should continue for a time sufficient to allow the adsorbent to collect a near equilibrium amount of the preferentially adsorbed compounds. The second basic step is the contacting of the adsorbent bearing both preferentially and non-preferentially adsorbed compounds with a material which displaces the latter from the adsorbent. The second step is performed in a manner which results in the adsorbent containing significant quantities of only the preferentially absorbed feed component and the material used to displace the non-preferentially adsorbed compounds.

The third basic step of the adsorptive separation process is the desorption of the preferentially adsorbed compounds. This may be performed by changing the conditions of temperature and pressure but in the subject process, it is performed by contacting the adsorbent with a desorbent stream. The desorbent stream contains a chemical compound capable of displacing or desorbing the preferentially adsorbed compounds from the adsorbent to thereby release these compounds and prepare the adsorbent for another adsorption step.

The contacting of the adsorbent with either the feed stream or the desorbent stream leaves the interstitial void spaces between the adsorbent particles filled with the components of these particular streams. When the next contacting step begins, this residual liquid is admixed into the entering liquid. This results in the effluent streams removed from the adsorbent bed being mixtures of compounds from the two or more streams which are passed into the adsorbent bed. In the subject process, two such effluent streams are produced. They comprise a mixture of the desorbent and the preferentially adsorbed chemical compounds and a mixture of the desorbent with the chemical compounds which are not preferentially absorbed. In order to obtain a high purity product stream of the preferentially adsorbed chemical compounds and to recover the desorbent, it is necessary to fractionate these two effluent streams. The two effluent streams are therefore fractionated in two separate fractionation columns referred to as the raffinate column and the extract column.

It is an objective of the subject invention to provide an improved process for the adsorptive separation of hydrocarbons or hydrocarbonaceous compounds. It is another objective of the invention to provide a hydrocarbon separation process utilizing a simulated moving bed of adsorbent. It is a further objective of the invention to provide an improved effluent fractionation method for use in a process for separating normal paraffinic hydrocarbons from a mixture of normal and isoparaffinic hydrocarbons.

The sequential adsorption and desorption steps of an adsorptive separatory process may be performed using a fixed bed of adsorbent having fixed inlet and outlet points at opposite ends of the adsorbent bed. However, certain benefits are obtained by using a simulated moving bed of adsorbent. These benefits include the continuous production of a high purity product stream. Preferably, the countercurrent flow of the bed of solid adsorbent and the various entering liquid streams, such as the feed and desorbent streams, is simulated.

Two separate actions are involved in this simulation. The first of these is the maintenance of a net fluid flow through the bed of adsorbent in a direction opposite to the direction of simulated movement of the adsorbent. This is performed through the use of a pump operatively connected in a manner to achieve this circulation along the length of the entire bed of adsorbent. The second action involved in simulating the movement of the adsorbent is the periodic actual movement of the location of the various zones, such as the adsorption zone, along the length of the bed of adsorbent. This actual movement of the location of the various zones is performed gradually in a unidirectional pattern by periodically advancing the points at which the entering streams enter the adsorbent bed and the points at which the effluent streams are withdrawn from the adsorbent bed. It is only the locations of the zones as defined by the respective feed and withdrawal points along the bed of adsorbent which are changed. The adsorbent bed itself is fixed and does not move.

The bed of adsorbent may be contained in one or more separate interconnected vessels. At a large number of points along the length of the bed of adsorbent, the appropriate openings and conduits are provided to allow the addition or withdrawal of liquid. At each of these points, there is preferably provided a constriction of the cross-section of the bed of adsorbent by a liquid distributor-collector. These may be similar to the apparatus described in U.S. Pat. Nos. 3,208,833; 3,214,247 and 3,523,762. These distributor-collectors serve to aid in the establishment and maintenance of plug flow of the fluids along the length of the bed of adsorbent. The two points at which any one stream enters and the corresponding effluent stream leaves the bed of adsorbent are separated from each other by at least two or more potential fluid feed or withdrawal points which are not being used. For instance, the feed stream may enter the adsorption zone at one point and flow past nine potential withdrawal points and through nine distributor-collectors before reaching the point at which it is withdrawn from the adsorbent bed as the raffinate stream.

The gradual and incremental movement of the adsorption zone is achieved by periodically advancing the actual points of liquid addition or withdrawal to the next available potential point. That is, in each advance of the adsorption zone, the boundaries marking the beginning and the end of each zone will move by the relatively uniform distance between two adjacent potential points of liquid addition or withdrawal. The majority of the zone is unaffected and remains intact since the zone extends past several of these fluid transfer points.

The switching of the fluid flows at these many different locations may be achieved by a multiple-valve manifold or by the use of a multiple-port rotary valve. A central digital controller is preferably used to regulate the operation of the rotary valve or manifold. For simplicity, only the actual points of liquid addition and withdrawal are represented in the Drawing and the large number of potential transfer points and the required interconnecting lines between the rotary valve and the bed of adsorbent have not been presented. Further details on the operation of a simulated moving bed of adsorbent and the preferred rotary valves may be obtained from the previously cited references and from U.S. Pat. Nos. 3,040,777; 3,422,848; 3,192,954 (all Cl. 137-625.15); 2,957,485; 3,131,232; 3,268,604 and 3,268,605.

The subject process can be practiced using any type of commercially operable and practical selective adsorbent. The preferred adsorbent comprises a shape selective zeolite commonly referred to as a molecular sieve. The term "shape selective" refers to the zeolite's ability to separate molecules according to size or shape because of the fixed and relatively uniform cross-sectional diameter of the zeolite's pore structure. The preferred zeolites comprise synthetic crystalline aluminosilicates. Since the pure zeolites are relatively soft and powdery, the commercially used molecular sieves comprise a binder such as clay or alumina to produce a stronger and more attrition-resistant adsorbent particle. The adsorbent particles preferably have a size range of about 20 to about 40 mesh.

The particular adsorbent utilized in the process will depend on the hydrocarbonaceous materials which it is desired to separate. For instance, type X or type Y which contain selected cations chosen from the Group I-A and Group II-A metals may be used to separate xylene isomers. The selective adsorption of olefinic hydrocarbons from saturated hydrocarbons may be performed using a copper-exchanged Type Y zeolite as described in U.S. Pat. No. 3,720,604. The adsorbents which are preferred for the separation of normal paraffinic hydrocarbons from isoparaffinic hydrocarbons have relatively uniform pore diameters of about 5 angstroms such as commercially available type 5A molecular sieves produced by the Linde Division of Union Carbide Corp.

Although adsorptive separation processes can be operated with both vapor-phase and liquid-phase conditions, the use of liquid-phase conditions is preferred. Adsorption-promoting conditions therefore include a pressure sufficient to maintain all of the chemical compounds present in the adsorbent bed as liquids. A pressure of from atmospheric to about 50 atmospheres may be employed with the pressure preferably being between 1.0 and 32 atmospheres gauge. Suitable operating temperatures range from 40° C. to about 250° C.

As used herein, the term "feed stream" is intended to indicate a stream in the process which comprises the feed material and which is charged to the bed of adsorbent for the purpose of recovering the extract component. The feed stream will comprise one or more extract components and one or more raffinate components. An "extract component" is a chemical compound which is preferentially adsorbed by the adsorbent which is being used as compared to a "raffinate component." Normally the term "extract component" is synonymous with the desired product of the process. For instance, in the preferred embodiment of the subject process, normal paraffins are selectively adsorbed compared to isoparaffins and are the extract component which is recovered as a product. The other chemical compounds which were contained in the feed stream, which in the preferred embodiment are mainly isoparaffins, become the raffinate components.

The term "extract stream" refers to a stream which contains extract components originally contained in the feed stream and which have been desorbed from the bed of adsorbent by the desorbent stream. The composition of the extract stream as it leaves the bed of adsorbent will normally vary with time and can range from about 100 mole percent extract components to about 100 mole percent desorbent components. The term "raffinate stream" is intended to indicate a stream originating at the bed of adsorbent and which contains the majority of the raffinate components of the feed stream. The raffinate stream is basically the unadsorbed components of the feed stream plus desorbent components which are picked up during passage through the adsorption zone. The composition of the raffinate stream as it leaves the bed of adsorbent will also vary with time from a high percentage of desorbent to a high percentage of raffinate components. Both the extract stream and the raffinate stream are normally passed into a backmixed accumulation zone before being passed into the respective fractionation columns.

As used herein, the term "desorbent" is intended to indicate a chemical compound capable of desorbing the extract component from the bed of adsorbent. A "desorbent stream" is a process stream in which the desorbent is carried to the bed of adsorbent. In the subject process, a multi-component desorbent stream is utilized. A multi-component flush stream is also passed into the bed of adsorbent in the subject process. As used herein, the term "flush stream" is intended to refer to a stream passed into the bed of adsorbent prior to the passage of the desorbent stream into adsorbent bed for the purpose of removing substantial amounts of the raffinate components of the feed stream from the interstitial void volume and non-selective pore volume of the adsorbent bed. The flush stream will contain a "flush component" which is sometimes referred to as a sweeping agent.

The feed stream to the normal paraffin recovery embodiments of the invention are hydrocarbon fractions having a carbon number range of from about 6 carbon atoms per molecule to about 30 carbon atoms per molecule. Preferably, the carbon number range of the feed stream is rather narrow and is from about 3 to 10 carbon numbers. A hydrotreated $C_{10}$ to $C_{15}$ kerosene fraction or a $C_{10}$ to $C_{20}$ gas oil fraction are representative feed streams. The feed stream may contain normal paraffins, isoparaffins and aromatics but is preferably free of olefins or has a very low olefin concentration. The concentration of normal paraffins in the feed stream may vary from about 15 to about 60 vol.%. The concentration of the aromatics is typically from about 10–30 vol.% but may be as low as 2–4 vol.%. These feed aromatics may be monocyclic aromatics such as benzene or alkylbenzenes and bicyclic aromatics including naphthalenes and biphenyls. The aromatic hydrocarbons have boiling points falling within the boiling point range of the desired extract components of the feed stream and are referred to as "co-boiling" aromatics.

During the adsorption of normal paraffins from the feed stream, a small but definite amount of the co-boiling aromatics present in the feed stream will be adsorbed on the external surfaces of the adsorbent particles. To minimize the amount of these aromatics which ultimately appear in the extract stream and therefore in the product of the process as impurities, an aromatic-selective desorbent is preferably present in the flush stream in addition to the flush component. This selective desorbent is referred to herein as the "first hydrocarbon" and also as the "first desorbent compound." The first desorbent compound is capable of desorbing surface-adsorbed feed aromatics but is not capable of desorbing feed normal paraffins from the adsorbent.

The aromatic-selective first desorbent compound is preferably an aromatic hydrocarbon which has a different boiling point than the feed mixture and the flush component of the flush stream to facilitate easy separation of the first desorbent compound from these materials. A $C_8$ aromatic, such as ethylbenzene of para-xylene, is specifically preferred for use during the separation of a $C_{10}$ to $C_{15}$ feed stream. The use of the selective first desorbent compound may be omitted if the presence of aromatic hydrocarbons in the extract stream is acceptable or if the feed stream does not contain aromatics. The first desorbent compound perferably has two fewer carbon atoms per molecule than the lowest molecular weight extract component of the feed stream which it is desired to recover. The concentration of the first desorbent compound in the flush stream may range from about 5 to about 100 vol.% but is preferably in the range of from 15 to 40 vol.%.

The flush component of the flush stream is preferably a raffinate-type compound which differs sufficiently in boiling point from the raffinate components of the feed stream. This allows it to be readily separated from the raffinate stream by fractionation. The flush component may be selected from the higher or lower boiling homologs of the isoparaffins or naphthenes in the feed stream. Isooctane is a preferred flush component for use in the separation of normal paraffins from a $C_{10}$ to $C_{15}$ feed stream or a similar fraction. The isooctane is not preferentially adsorbed by the adsorbent and is easily fractionated from the $C_{10}$ to $C_{15}$ raffinate components of the raffinate stream. The flush component is referred to herein as the "second hydrocarbon."

The selectively adsorbed normal paraffinic hydrocarbons are removed from the adsorbent through the use of a second desorbent compound. The second desorbent compound is also referred to herein as the "third hydrocarbon." The second desorbent may comprise any normal paraffin having a boiling point different from the normal paraffins in the feed stream and which is a free flowing liquid at process conditions. Preferably, the second desorbent compound has a lower boiling point and has fewer carbon atoms per molecule than the first desorbent compound or the flush compound. Normal pentane is preferred as the second desorbent compound for the recovery of normal paraffins having 9 or more carbon atoms per molecule. The desorbent stream of the subject process preferably comprises an admixture of the second desorbent compound and the flush compound. That is, desorbent stream in this instance is preferably an admixture of the second and third hydrocarbons. The concentration of the second desorbent compound in this admixture is preferably within the range of from 40 to 80 vol.%. The desorbent stream should contain little or none of the first desorbent compound. Preferably, the concentration of the first desorbent compound in the desorbent stream is less than 0.1 vol.%.

The extract and the raffinate streams are each passed into an intermediate point of a separate fractionation column. That is, the feed point to the column is separated from both extremities of the column by at least four fractionation trays. In the subject process, the raffinate components of the raffinate stream are the heaviest (highest boiling) materials fed to the raffinate column and the extract components of the extract stream are the heaviest materials fed to the extract column. The raffinate components of the raffinate stream are therefore drawn off the bottom of the raffinate column and may be withdrawn from the process. In a similar manner, the extract components of the extract stream are removed from the process as the net bottoms stream of the extract column.

In the preferred embodiment of the invention, the extract stream and the raffinate stream comprise both the first and the second desorbent compounds and the flush compound. All three of these compounds move upward through the respective columns to points above the feed point. The overhead vapor removed from the extract column and the raffinate column would therefore be a mixture of all three components unless another separation is performed. In order to recycle these components to the adsorbent, it is necessary to further separate them into the previously described desired two component admixtures.

According to the inventive concept, the separation required to produce the desorbent stream and the flush stream is performed by removing a liquid sidecut from an upper intermediate point of each column and passing the sidecut into a stripping column. The sidecut streams will contain an equilibrium mixture of all compounds present at the drawoff point, which is separated from the feed point by the number of fractionation trays required to ensure the extract and raffinate components are not present in the sidecuts. The stripping columns are operated at conditions effective to reject essentially all of the lowest boiling hydrocarbon present in the sidecut stream in an overhead vapor stream and to therefore produce a net bottoms stream essentially free of this lowest boiling component.

The overhead vapor stream of each stripping column is passed into the column from which the sidecut was removed. The heat content of the stripping column overhead vapor is thereby utilized within the extract column and the raffinate column. This heat is used to improve the separation performed in the upper sections of these columns and is not rejected into a separate overhead condenser as in the prior art fractionation systems. The subject process therefore is an improvement over the prior art and increases the efficiency of heat utilization within the overall hydrocarbon separation process.

The upper section of the raffinate column and of the extract column are operated at conditions at which the overhead vapor of these columns is essentially free of the highest boiling point component of the sidecut stream. The overhead product of these two columns therefore comprises the two lowest boiling compounds in the group composed of the first desorbent compound, the second desorbent compound and the flush compound. In the preferred embodiment of the invention, each of the sidecut streams comprises a $C_8$ aromatic, normal pentane and isooctane. The overhead vapor and net overhead liquid of the raffinate and extract columns then comprise normal pentane and isooctane and the bottoms stream of the stripping columns comprise isooctane and the $C_8$ aromatic.

Although the overhead streams of the raffinate column and the extract column contain the same two compounds the composition of these two streams may be different due to different concentrations of the two components in the extract and raffinate streams. The ratio of the two high boiling components in the bottoms streams of the stripping columns may also be unequal. The net overhead streams of the raffinate column and the extract column are combined to form the desorbent stream charged to the adsorbent bed via the rotary valve. The net bottoms streams of the two stripping columns are admixed to form the flush stream which is passed into the adsorbent bed. A portion of either of these two admixtures may be withdrawn as a drag stream to prevent the buildup of impurities or to adjust the composition or quantity of desorbent and flush material in the process.

In accordance with this description, the invention may be characterized as a process for separating hydrocarbons which comprises the steps of passing a feed stream comprising an isoparaffinic hydrocarbon having more than 9 carbon atoms per molecule, normal paraffinic hydrocarbon having the same number of carbon atoms as the isoparaffinic hydrocarbon and a coboiling aromatic hydrocarbon into a fixed bed of solid adsorbent comprising a crystalline aluminosilicate which preferentially adsorbs normal paraffinic hydrocarbons and aromatic hydrocarbons relative to isoparaffinic hydrocarbons of the same carbon number and effecting the selective retention of the normal paraffinic hydrocarbon and aromatic hydrocarbon within an adsorption zone within the bed of solid adsorbent; passing a flush stream comprising a first and a second hydrocarbon into the bed of solid adsorbent at a different point than the feed stream is passed into the bed of solid adsorbent; passing a desorbent stream comprising the second hydrocarbon and a third hydrocarbon into the fixed bed of solid adsorbent at a different point than the feed stream or the flush stream are passed into the fixed bed of solid adsorbent and through a desorption zone; withdrawing an extract stream comprising the preferentially adsorbed normal paraffinic hydrocarbon, the first, the second and the third hydrocarbons from the fixed bed of solid adsorbent; withdrawing a raffinate stream comprising the isoparaffinic hydrocarbon, the coboiling aromatic hydrocarbon, the first, the second and the third hydrocarbons from the fixed bed of solid adsorbent; simulating the utilization of a moving bed of the solid adsorbent by maintaining a net fluid flow through the fixed bed of solid adsorbent and by periodically moving in a unidirectional pattern the points at which the feed stream and the desorbent stream are passed into the fixed bed of solid adsorbent and the points at which the extract stream and the raffinate stream are withdrawn from the fixed bed of solid adsorbent to gradually shift the location of the adsorption and desorption zones within the bed of solid adsorbent; separating the extract stream in a first fractionation column into a first overhead fraction comprising the second and the third hydrocarbons, a first sidecut fraction comprising the first, the second and the third hydrocarbons and a first bottoms fraction comprising the preferentially adsorbed normal paraffinic hydrocarbon; separating the first sidecut fraction in a second fractionation column into a second bottoms fraction comprising the first and the second hydrocarbons and a first overhead vapor stream comprising the second and the third hydrocarbons; passing the first overhead vapor stream into an intermediate point of the first fractionation column; separating the raffinate stream in a third fractionation column into a second overhead fraction comprising the second and the third hydrocarbons, a second sidecut fraction comprising the first, the second, and the third hydrocarbons and a third bottoms fraction comprising the isoparaffinic hydrocarbon and the aromatic hydrocarbon; separating the second sidecut fraction in a fourth fractionation column into a fourth bottoms fraction comprising the first and the second hydrocarbons and a second overhead vapor stream comprising the second and the third hydrocarbons; passing the second overhead vapor stream into an intermediate point of the third fractionation column; passing in admixture at least a portion of each of the third and the fourth bottoms fractions into a bed of solid adsorbent as the previously referred to flush stream; and passing in admixture at least a portion of each of the first and the second overhead fractions into a bed of solid adsorbent as the previously referred to desorbent stream.

EXAMPLE

The following example is intended to further illustrate the subject process. A feed stream derived from a hydrotreated kerosene having a flow rate of about 5695 barrels per stream day (BPSD) is charged to a fixed bed adsorption zone located in two vertical chambers through a rotary valve. The feed stream is passed into the adsorption zone at a temperature of about 350° F. (177° C.) and a pressure of about 350 psig. (24.8 atm.). The use of a moving bed of adsorbent is simulated as described above. The feed stream contains about 92 moles per hour (mph) of $C_{10}$ to $C_{14}$ normal paraffins and various other hydrocarbons having the same boiling point range as the normal paraffins. These other hydrocarbons in the feed stream include about 93 mph of cyclic paraffins, 143 mph of isoparaffins and 78 mph of aromatics. The desorbent stream charged to the rotary valve is a mixture of isooctane and n-pentane having a flow rate of about 790 mph. The flush stream passed into the rotary valve is a mixture of isooctane and $C_8$ aromatics having a flow rate of about 190 mph. The flush stream and the desorbent stream are charged to the rotary valve at the same temperature and pressure as the feed stream.

The raffinate stream removed from the adsorption zone is passed through a mixing drum to smooth out composition fluctuations and then into the raffinate column. The flow scheme of the process is similar to that shown in the Drawing. This column is operated at an overhead pressure of about 20 psig. (1.36 atm.) and an overhead vapor temperature of about 101° C. The net overhead stream removed from the raffinate column comprises approximately 281 mph of n-pentane and isooctane. The sidecut stream has a flow rate of about 150 mph and comprises n-pentane, isooctane and $C_8$ aromatics. The net bottoms stream of the raffinate column contains about 4 mph of normal $C_{10}$ to $C_{14}$ paraffins and about 312 mph of raffinate components of the feed stream.

The extract stream is also passed through a mixing drum and is then passed into the extract column. This column is also operated at an overhead pressure of about 20 psig. (1.36 atm.) and an overhead vapor temperature of about 101° C. The net overhead stream removed from the extract column is a mixture of n-pentane and isooctane having a flow rate of about 428 mph. The extract column sidecut stream has a flow rate of about 203 mph and contains n-pentane, isooctane and $C_8$-aromatics. The sidecut stream is removed 14 fractionation trays above the feed point and is passed into a stripping column. This stripping column and the stripping column which receives the raffinate column sidecut stream are operated at conditions set by the temperature and pressure of the sidecut streams. The extract column sidecut stream is removed at a temperature of 122° C. and a pressure of about 22 psig. (1.50 atm.). The overhead vapor removed from the top of the extract column sidecut stripper has a temperature of 122° C. Both stripping columns have ten fractionation trays. The net bottoms stream of the extract column is removed at a temperature of about 256° C. and contains about 87 mph of $C_{10}$ to $C_{14}$ normal paraffins recovered from the feed stream. This net bottoms stream also contains about 1 mph of $C_{10}$ to $C_{14}$ cyclic and isoparaffinic hydrocarbons.

I claim as my invention:
1. In a process for the separation of chemical compounds wherein:
   (a) a feed stream is passed into a fixed bed of a solid adsorbent which preferentially adsorbs one component species contained in the feed stream;
   (b) a multi-component desorbent stream is passed into the fixed bed of solid adsorbent at a different point than the feed stream is passed into the fixed bed of solid adsorbent;
   (c) a multi-component flush stream is passed into the fixed bed of solid adsorbent at a different point than the feed stream or the desorbent stream are passed into the fixed bed of solid adsorbent;
   (d) an extract stream which is rich in the preferentially adsorbed component species and a raffinate stream are withdrawn from the bed of solid adsorbent;
   (e) a net fluid flow is maintained through the fixed bed of solid adsorbent, and the points at which the feed stream and the desorbent stream are passed into the bed of solid adsorbent and the points at which the extract stream and the raffinate stream are withdrawn from the bed of solid adsorbent are periodically moved in a unidirectional pattern which simulates the utilization of a moving bed of the adsorbent by gradually shifting the location of adsorption and desorption zones within the bed of solid adsorbent;
   (f) the extract stream is passed into a first fractionation column and separated into a first multi-component overhead fraction, a first multi-component sidecut fraction and a first bottoms fraction;
   (g) the raffinate stream is passed into a second fractionation column and separated into a second multi-component overhead fraction, a second multi-component sidecut fraction and a second bottoms fraction; the improvement which comprises:
      (i) passing the first sidecut fraction into a third fractionation column and therein separating the first sidecut fraction into a third bottoms fraction and a first overhead vapor stream which is passed into an intermediate point of the first fractionation column;

(ii) passing the second sidecut fraction into a fourth fractionation column and therein separating the second sidecut fraction into a fourth bottoms fraction and a second overhead vapor stream which is passed into an intermediate point of the second fractionation column; and, (iii) passing in admixture at least a portion of each of the third and the fourth bottoms fractions into the bed of solid adsorbent as the previously specified flush stream of step (c).

2. A process for separating hydrocarbons which comprises the steps of:

(a) passing a feed stream comprising an isoparaffinic hydrocarbon having more than 9 carbon atoms per molecule, a normal paraffinic hydrocarbon having the same number of carbon atoms as the isoparaffinic hydrocarbon, and a co-boiling aromatic hydrocarbon into a fixed bed of a solid adsorbent comprising a crystalline aluminosilicate which preferentially adsorbs normal paraffinic hydrocarbons and aromatic hydrocarbons and effecting the selective retention of the normal paraffinic hydrocarbon and aromatic hydrocarbon within an adsorption zone within the bed of solid adsorbent;

(b) passing a flush stream comprising a first and a second hydrocarbon into the bed of solid adsorbent at a different point than the feed stream is passed into the bed of solid adsorbent;

(c) passing a desorbent stream comprising the second hydrocarbon and a third hydrocarbon into the fixed bed of solid adsorbent at a different point than the feed stream or the flush stream are passed into the fixed bed of solid adsorbent and through a desorption zone;

(d) withdrawing an extract stream comprising the preferentially adsorbed normal paraffinic hydrocarbon, the first, the second and the third hydrocarbons from the fixed bed of solid adsorbent;

(e) withdrawing a raffinate stream comprising the isoparaffinic hydrocarbon, the co-boiling aromatic hydrocarbon, the first, the second and the third hydrocarbons from the fixed bed of solid adsorbent;

(f) simulating the utilization of a moving bed of the solid adsorbent by maintaining a net fluid flow through the fixed bed of solid adsorbent and by periodically moving in a unidirectional pattern the points at which the feed stream and the desorbent stream are passed into the fixed bed of solid adsorbent and the points at which the extract stream and the raffinate stream are withdrawn from the fixed bed of solid adsorbent to gradually shift the location of the adsorption and desorption zones within the bed of solid adsorbent;

(g) separating the extract stream in a first fractionation column into a first overhead fraction comprising the second and the third hydrocarbons, a first sidecut fraction comprising the first, the second and the third hydrocarbons and a first bottoms fraction comprising the preferentially adsorbed normal paraffinic hydrocarbon;

(h) separating the first sidecut fraction in a second fractionation column into a second bottoms fraction comprising the first and the second hydrocarbons and a first overhead vapor stream comprising the second and the third hydrocarbons;

(i) passing the first overhead vapor stream into an intermediate point of the first fractionation column;

(j) separating the raffinate stream in a third fractionation column into a second overhead fraction comprising the second and the third hydrocarbons, a second sidecut fraction comprising the first, the second, and the third hydrocarbons and a third bottoms fraction comprising the isoparaffinic hydrocarbons and the aromatic hydrocarbon;

(k) separating the second sidecut fraction in a fourth fractionation column into a fourth bottoms fraction comprising the first and the second hydrocarbons and a second overhead vapor stream comprising the second and the third hydrocarbons;

(l) passing the second overhead vapor stream into an intermediate point of the third fractionation column;

(m) passing in admixture at least a portion of each of the third and the fourth bottoms fractions into the bed of solid adsorbent as the flush stream referred to in step (b); and, (n) passing in admixture at least a portion of each of the first and the second overhead fractions into the bed of solid adsorbent as the desorbent stream referred to in step (c).

3. The process of claim 2 further characterized in that the first hydrocarbon is an aromatic hydrocarbon having at least two less carbon atoms per molecule than the preferentially adsorbed normal paraffinic hydrocarbon.

4. The process of claim 3 further characterized in that the second hydrocarbon is an isoparaffinic hydrocarbon having the same number of carbon atoms as the first hydrocarbon.

5. The process of claim 4 further characterized in that the third hydrocarbon is a normal paraffinic hydrocarbon having at least two less carbon atoms per molecule than the second hydrocarbon.

6. The process of claim 5 further characterized in that the preferentially adsorbed normal paraffinic hydrocarbon has from 10 to 14 carbon atoms per molecule.

* * * * *